(12) United States Patent
Lorant

(10) Patent No.: US 8,758,736 B2
(45) Date of Patent: Jun. 24, 2014

(54) WATER-IN-OIL (W/O) EMULSION STABILIZED WITH A LIPOPHILIC EMULSIFIER AND A HYDROPHOBICALLY MODIFIED POLYSACCHARIDE

(75) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 319 days.

(21) Appl. No.: 12/809,869

(22) PCT Filed: Dec. 17, 2008

(86) PCT No.: PCT/EP2008/067768
§ 371 (c)(1),
(2), (4) Date: Oct. 14, 2010

(87) PCT Pub. No.: WO2009/080657
PCT Pub. Date: Jul. 2, 2009

(65) Prior Publication Data
US 2011/0020258 A1    Jan. 27, 2011

Related U.S. Application Data

(60) Provisional application No. 61/021,047, filed on Jan. 15, 2008.

(30) Foreign Application Priority Data

Dec. 20, 2007 (FR) ...................... 07 60167
Feb. 18, 2008 (FR) ...................... 08 51016

(51) Int. Cl.
*A61Q 1/14* (2006.01)
*A61Q 1/04* (2006.01)
*A61Q 5/00* (2006.01)
*A61Q 19/00* (2006.01)

(52) U.S. Cl.
USPC ........ 424/78.02; 424/64; 424/70.13; 424/401

(58) Field of Classification Search
None
See application file for complete search history.

(56) References Cited

U.S. PATENT DOCUMENTS

2005/0031560 A9 * 2/2005 Simonnet et al. ............... 424/63
2005/0031580 A1   2/2005 Allef et al.

FOREIGN PATENT DOCUMENTS

| EP | 1 813 267 | | 8/2007 |
| JP | 2003-104825 | * | 4/2003 |
| WO | WO 2007/017196 | * | 2/2007 |

OTHER PUBLICATIONS

Meyer, J. et al., "A Novel PEG-Free Emulsifier Designed for Formulating W/O Lotions With a light Skin Feel", SOFW Journal, vol. 131, No. 11, pp. 20-22, 24-26 and 28, (2005) XP 009104229.
U.S. Appl. No. 12/809,835, filed Jun. 21, 2010, Lorant.
U.S. Appl. No. 12/809,833, filed Jun. 21, 2010, Lorant.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

The invention relates to a composition in the form of a water-in-oil emulsion comprising an aqueous phase dispersed in an oily phase and containing: a) at least one fatty acid ester of a polyol; and b) at least one hydrophobically modified polysaccharide chosen from inulins, celluloses and derivatives thereof, starches and agars, and mixtures thereof. In particular, the fatty acid ester of a polyol is polyglyceryl-4 diisostearate/polyhydroxystearate/-sebacate. It also relates to a process for caring for, making up and/or removing makeup from the skin, including the scalp, the hair and the lips, comprising the topical application of such a composition to the skin, the scalp or the lips.

11 Claims, No Drawings

WATER-IN-OIL (W/O) EMULSION STABILIZED WITH A LIPOPHILIC EMULSIFIER AND A HYDROPHOBICALLY MODIFIED POLYSACCHARIDE

The field of the invention relates to stable compositions in the form of water-in-oil emulsions.

The compositions according to the invention are preferably natural.

The term "natural compositions" is intended to mean, according to the invention, compositions comprising predominantly or even exclusively ingredients of natural origin, as opposed to ingredients of petrochemical or synthetic origin.

The invention relates in particular to a composition in the form of a water-in-oil emulsion comprising an aqueous phase dispersed in an oily phase, and containing:
 a) at least one fatty acid ester of a polyol, and
 b) at least one hydrophobically modified polysaccharide chosen from inulins, celluloses and derivatives thereof, starches and agars, and mixtures thereof.

In particular, the fatty acid ester of a polyol is polyglyceryl-4 diisostearate/polyhydroxystearate/-sebacate.

The composition according to the invention has the advantage of being very stable over time and pleasing to the senses, even in the absence of any fatty substance of petrochemical and/or synthetic nature (silicones, volatile oils of synthetic origin such as branched hydrocarbons and cyclic silicones).

This composition can be used in particular in the cosmetics and/or dermatological fields and constitutes in particular a care and/or makeup and/or makeup-removing product for the skin and/or its appendages, which also gives a soft feel when applied to the skin and/or its appendages.

The term "skin" is also intended to mean the scalp and the semi-mucous membranes (lips).

The term "appendages" is intended to mean in particular the hair, the eyelashes and the nails.

Compositions, in particular cosmetic compositions, based on ingredients of natural origin are increasingly being sought. However, the preparation of "all natural" compositions, i.e. in particular free of ingredients of synthetic origin, encounters problems of formulation both in terms of long-term stability and in terms of the sensory properties on application. Furthermore, this is even more essential for water-in-oil emulsions, which are known to be more difficult to stabilize and which generally have a greasy, heavy and sticky feel on application.

Moreover, water-in-oil emulsions free of synthetic fatty substances (such as cyclic silicones or branched hydrocarbons) are generally soapy on application, heavy, sticky and rough on the skin.

There remains therefore the need for compositions in the form of a water-in-oil emulsion, which are in particular natural and which are stable over time and provide pleasant cosmetic properties such as a certain lightness and softness on application without soaping effects (white film on application to the skin).

The term "stability over time" is herein intended to mean the ability to render a water-in-oil emulsion homogeneous and even, and one which does not undergo phase separation (separation of the aqueous phase and of the oily phase) or release oil, at least for two months at 37° C., or even two months at 45° C.

The applicant has shown, surprisingly, that the use of a fatty acid ester of a polyol, and in particular the use of polyglyceryl-4 diisostearate/polyhydroxy-stearate/sebacate, in combination with at least one particular hydrophobically modified polysaccharide, makes it possible to obtain W/O emulsions which are stable in the long term and which also have good sensory properties, in particular:
 little whitening on application, even in the absence of silicones or other volatile oils of synthetic origin;
 in the end leaving the skin soft.

The compositions according to the invention are particularly advantageous in the cosmetics or dermatological fields, especially in the skincare, photoprotection, makeup or makeup-removing field.

The invention relates especially to a composition in the form of a water-in-oil (W/O) emulsion comprising an aqueous phase dispersed in an oily phase and containing:
 a) at least one fatty acid ester of a polyol; and
 b) at least one hydrophobically modified polysaccharide chosen from inulins, celluloses and derivatives thereof, starches and agars, and mixtures thereof.

The invention relates in particular to a composition in the form of a water-in-oil (W/O) emulsion comprising:
 a) an oily continuous phase containing at least one fatty acid ester of a polyol;
 b) an aqueous phase, and
 c) at least one hydrophobically modified polysaccharide chosen from inulins, celluloses and derivatives thereof, starches and agars, and mixtures thereof.

The aqueous phase is dispersed in the oily phase with stirring.

Generally, the hydrophobically modified polysaccharide is in the aqueous phase. In certain specific cases (for example: hydrophobically modified inulin), the hydrophobic polysaccharide may also be dispersed in the oily phase, before the emulsification.

Fatty Acid Esters of Polyols

According to the invention, the term "fatty acid esters of polyols" is intended to mean esters of a fatty acid (or fatty acid polymers) and of a polyol, in which the fatty acid comprises a $C_6$-$C_{22}$, preferably $C_{16}$-$C_{20}$, alkyl chain and the polyol is chosen from glycerol, a polyglycerol and sorbitan, and mixtures thereof. The fatty acid may also be in a polymeric form, as is the case of polyhydroxystearic acid (polymer of 12-hydroxystearic acid).

According to one particular embodiment, the fatty acid ester of a polyol is a $C_{16}$-$C_{20}$ fatty acid ester of glycerol and/or of sorbitan, and mixtures thereof.

As examples of fatty acids with a linear or branched $C_{16}$-$C_{20}$ chain, mention may be made of stearic acid, isostearic acid, lauric acid, myristic acid and palmitic acid. As an example of a $C_{16}$-$C_{20}$ fatty acid polymer, mention may be made of poly(12-hydroxystearic acid).

Preferably, stearic acid, isostearic acid, poly(12-hydroxy acid) and mixtures thereof will be used.

The term "polyglycerols" is intended to mean compounds of formula

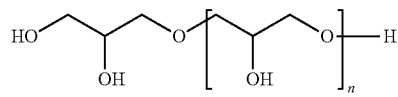

in which the degree of condensation n ranges from 1 to 11, preferably from 2 to 6 and even more preferably from 3 to 6.

According to one particular embodiment, the fatty acid ester of a polyol contains 2 to 10 mol (units) of polyols, preferably 2 to 4 mol of polyols, in particular 2 to 4 units of glycerol or a mixture of polyglycerols (glycerol, di-, tri-, tetra-, penta-, oligoglycerols).

Even more preferably, the fatty acid ester of a polyol contains 4 mol (or units) of a polyol, in particular 4 mol (or units) of glycerol.

According to one preferred embodiment, said fatty acid ester of a polyol is in addition a fatty acid ester of a dicarboxylic acid containing from 2 to 16 carbon atoms, preferably from 8 to 14 carbon atoms, such as azelaic acid, sebacic acid or dodecanedioic acid, and preferably sebacic ($C_{10}$) acid, and of a polyol.

By way of examples of fatty acid esters of a polyol that can be used in the composition of the invention, mention may be made of isostearic acid esters of polyols and mixtures thereof, in particular isostearic acid esters of glycerol and/or of sorbitan, for instance the polyglycerolated (4 mol) isostearate (INCI name: Polyglyceryl-4 isostearate) sold under the name Isolan G134® by the company Goldschmidt, the polyglycerolated (3 mol) diisostearate sold under the name Lameform TGI® by the company Cognis; the polyglycerolated (2 mol) distearate sold under the name Emalex PGSA® by the company Nihon emulsion; the polyglycerolated (10 mol) monoisostearate sold under the name Nikkol decaglyn 1-IS by the company Nihon Surfactant (INCI name: Polyglyceryl-10 isostearate); the polyglyceryl-4 diisostearate/polyhydroxystearate/-sebacate sold under the name Isolan GPS by Goldschmidt; the mixture of sorbitan isostearate and glyceryl isostearate, such as the product sold under the name Arlacel 986 by the company ICI, the mixture of sorbitan isostearate and polyglyceryl (3 mol) isostearate sold under the name Arlacel 1690 by the company Uniqema, and mixtures thereof.

As fatty acid esters of polyglycerol that are preferred according to the invention, mention may in particular be made of: the polyglycerolated (4 mol) isostearate (INCI name: Polyglyceryl-4 isostearate) sold under the name Isolan GI34® by Goldschmidt, the polyglyceryl-4 diisostearate/polyhydroxystearate/sebacate sold under the name Isolan GPS® by Goldschmidt, the mixture of sorbitan isostearate and polyglyceryl (3 mol) isostearate sold under the name Arlacel 1690® by the company Uniqema, and mixtures thereof.

According to one preferred embodiment of the invention, the fatty acid ester of a polyol according to the invention is an ester of poly(12-hydroxystearic acid) and of dicarboxylic acids obtained by esterification of a mixture of polyglycerol with (i) a polyhydroxystearic acid, with from 1 to 10, preferably from 2 to 8, even more preferably from 2 to 5 units of polyglycerol (preferably 4 units); (ii) linear or branched, aliphatic dicarboxylic acids containing from 2 to 16 carbon atoms, preferably from 4 to 14 carbon atoms (preferably sebacic acid); and (iii) saturated or unsaturated, linear or branched fatty acids containing from 6 to 22 carbon atoms, preferably from 16 to 20 carbon atoms (preferably isostearic acid).

Advantageously, the degree of esterification of the polyglycerol mixture is between 20% and 40%, preferably between 40% and 70%.

Such poly(12-hydroxystearic acid) esters of polyglycerol are described in application US 2005/0031580.

According to one preferred embodiment, the fatty acid ester of a polyol is an ester of poly(12-hydroxystearic acid) and of dicarboxylic acids obtained by esterification of a mixture of polyglycerol with (i) a polyhydroxystearic acid, with from 2 to 5 units of polyglycerol; (ii) linear or branched, aliphatic dicarboxylic acids containing 4 to 14 carbon atoms, and (iii) saturated or unsaturated, linear or branched fatty acids containing from 16 to 20 carbon atoms.

Preferably, the fatty acid ester of a polyol is an ester of polyhydroxystearic acid and of dicarboxylic acids obtained by esterification of a mixture of polyglycerol with (i) a polyhydroxystearic acid, with from 2 to 5 units of polyglycerol (preferably 4 units); (ii) linear or branched, aliphatic dicarboxylic acids containing 4 to 14 carbon atoms (preferably sebacic acid), and (iii) saturated or unsaturated, linear or branched fatty acids containing from 16 to 20 carbon atoms (preferably isostearic acid).

As a preferred example of a polyhydroxystearic acid ester of polyglycerol, mention may be made of polyglyceryl-4 diisostearate/polyhydroxystearate/-sebacate of formula

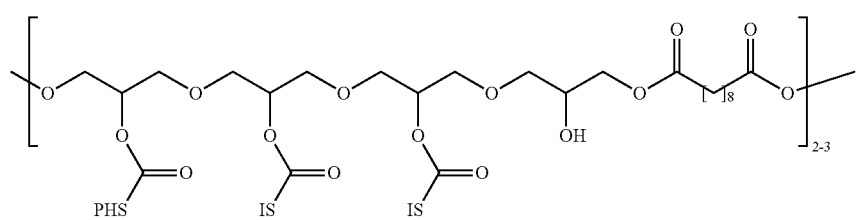

where PHS denotes polyhydroxystearic acid and IS denotes isostearic acid.

Such a compound is prepared according to application US 2005/0031580 and sold under the name Isolan GPS® by the company Goldschmidt (Degussa).

Even more preferably, the polyglyceryl-4 diisostearate/polyhydroxystearate/sebacate sold under the name Isolan GPS® by Goldschmidt will be used in the composition of the invention.

The content of fatty acid ester of a polyol in the composition according to the invention will be adjusted to the aqueous and oily phase contents of the composition according to the invention.

This content of fatty acid ester of a polyol will in particular range from 0.1% to 15% by weight relative to the total weight of the composition, in particular from 0.5% to 15%, preferably from 1% to 5%, and even more preferably from 1.5% to 3.5% by weight, relative to the total weight of the composition.

Hydrophobically Modified Polysaccharide

The term "hydrophobically modified polysaccharide" according to the invention is intended to mean especially a polysaccharide modified with hydrophobic chains, in particular modified by grafting of hydrophobic chains onto the hydrophilic backbone of said polysaccharide.

The hydrophobically modified polysaccharide of the composition according to the invention is chosen from inulins, celluloses and derivatives thereof (such as, for example, methylcelluloses, hydroxyalkylcelluloses, hydroxyethylcelluloses, hydroxypropylcelluloses, ethylhydroxyethylcelluloses, carboxymethylcelluloses), starches and agars, and mixtures thereof.

Preferably, inulins, celluloses and derivatives thereof, and mixtures thereof will be used.

Hydrophobically Modified Inulins

According to a first embodiment, the polysaccharide used in the present invention is chosen from fructans, in particular inulins.

Fructans or fructosans are oligosaccharides or polysaccharides comprising a series of anhydrofructose units optionally combined with one or more saccharide residues different from fructose. The fructans may be linear or branched. The fructans may be products obtained directly from a plant or microbial source or else products of which the chain length has been modified (increased or reduced) by fractionation, synthesis or hydrolysis, in particular enzyme hydrolysis. The fructans generally have a degree of polymerization of from 2 to approximately 1000, and preferably from 2 to approximately 60.

Three groups of fructans stand out. The first group corresponds to products in which the fructose units are for the most part linked by β-2-1 linkages. These are essentially linear fructans such as inulins.

The second group also corresponds to linear fructoses, but the fructose units are essentially linked by β-2-6 linkages. These products are levans. The third group corresponds to mixed fructans, i.e. fructans having β-2-6 and β-2-1 sequences. These are essentially branched fructans such as graminans.

The fructans used in the compositions according to the invention are inulins. Inulin can be obtained, for example, from chicory, from dahlia or from Jerusalem artichoke. Preferably, the inulin used in the composition according to the invention is obtained, for example, from chicory.

The polysaccharides, in particular the inulins, used in the compositions according to the invention are hydrophobically modified. In particular, they are obtained by grafting hydrophobic chains onto the hydrophilic backbone of the fructan.

The hydrophobic chains that can be grafted onto the main chain of the fructan may in particular be saturated or unsaturated, linear or branched hydrocarbon-based chains containing from 1 to 50 carbon atoms, such as alkyl, arylalkyl, alkylaryl or alkylene groups; divalent cycloaliphatic groups or organopolysiloxane chains. These hydrocarbon-based or organopolysiloxane chains may in particular comprise one or more ester, amide, urethane, carbamate, thiocarbamate, urea, thiourea and/or sulphonamide functions, such as, in particular, methylenedicyclohexyl and isophorone; or divalent aromatic groups such as phenylene.

The invention therefore relates to a composition in which the hydrophobically modified polysaccharide is an inulin modified with saturated or unsaturated, linear or branched hydrophobic chains containing from 1 to 50 carbon atoms, such as alkyl, arylalkyl, alkylaryl or alkylene groups; divalent cycloaliphatic groups or organopolysiloxane chains comprising one or more ester, amide, urethane, carbamate, thiocarbamate, urea, thiourea and/or sulphonamide functions, such as, in particular, methylenedicyclohexyl and isophorone; or divalent aromatic groups such as phenylene.

In particular, the inulin is obtained from chicory.

In particular, the polysaccharide, in particular the inulin, has a degree of polymerization of from 2 to approximately 1000, and preferably from 2 to approximately 60, and a degree of substitution of less than 2 on the basis of a fructose unit.

According to one preferred embodiment, the hydrophobic chains have at least one alkyl carbamate group of formula R—NH—CO— in which R is an alkyl group containing from 1 to 22 carbon atoms.

According to a more preferred embodiment, the hydrophobic chains are lauryl carbamate groups.

In particular, by way of nonlimiting illustration of the hydrophobically modified inulins that can be used in the compositions according to the invention, mention may be made of stearoyl inulin, such as those sold under the names Lifidrem INST by the company Engelhard and Rheopearl INS by the company Ciba; palmitoyl inulin; undecylenoyl inulin, such as those sold under the names Lifidrem INUK and Lifidrem INUM by the company Engelhard; and inulin lauryl carbamate, such as that sold under the name Inutec SP1 by the company Orafti.

In particular, the hydrophobically modified polysaccharide is a lauryl carbamate-grafted inulin, especially derived from the reaction of lauryl isocyanate with an inulin, in particular derived from chicory. By way of example of these compounds, mention may in particular be made of the product sold under the name Inutec SP1 by the company Orafti.

Hydrophobically Modified Cellulose Derivatives

According to another embodiment of the invention, the hydrophobically modified polysaccharide is a hydroxy($C_1$-$C_3$)alkylcellulose modified with hydrophobic chains, in particular hydrophobic group(s) containing from 8 to 30 carbon atoms.

The hydrophobically modified cellulose derivatives according to the invention are substituted with one or more aliphatic or aromatic, saturated or unsaturated, linear, branched or cyclic $C_8$-$C_{30}$ hydrocarbon-based chain(s).

According to one embodiment, the hydrophobic substituent(s) used is (are) $C_8$-$C_{30}$, preferably $C_{10}$-$C_{22}$, alkyl, arylalkyl or alkylaryl groups.

Preferably, the hydrophobic substituent(s) according to the present invention is (are) $C_{10}$-$C_{22}$, preferably $C_{16}$-$C_{20}$, saturated alkyl chains, such as cetyl ($C_{16}$), stearyl ($C_{18}$) or behenyl ($C_{20}$) groups.

According to one preferred embodiment, the hydrophobic substituent(s) according to the present invention is (are) a cetyl group or groups.

These cellulose derivatives with one or more hydrophobic substituent(s) according to the invention have a viscosity of preferably between 100 and 100 000 mPa·s, and preferably between 200 and 20 000 mPa·s, measured at 25° C. in a 1% by weight solution of polymer in water, this viscosity being determined conventionally using a Brookfield LVT viscometer at 6 rpm with the No. 3 spindle.

Among the cellulose derivatives with one or more hydrophobic substituent(s) that can be used in the compositions of the invention, mention may preferably be made of the cetyl hydroxyethylcelluloses sold under the names Natrosol Plus Grade 330 CS and Polysurf 67 CS (INCI: Cetyl Hydroxyethylcellulose) by the company Aqualon/Hercules.

The hydrophobically modified polysaccharide is present in the composition according to the invention at a content ranging from 0.01% to 20% by weight relative to the total weight of the composition, preferably from 0.05% to 15% by weight, more preferably from 0.1% to 5% by weight, and even more preferably from 0.5% to 3%, or even from 0.1% to 1% by weight, relative to the total weight of the composition.

According to one preferred embodiment, the composition according to the invention comprises:

a fatty acid ester of a polyol, chosen from polyglyceryl-4 diisostearate/polyhydroxystearate/-sebacate of formula

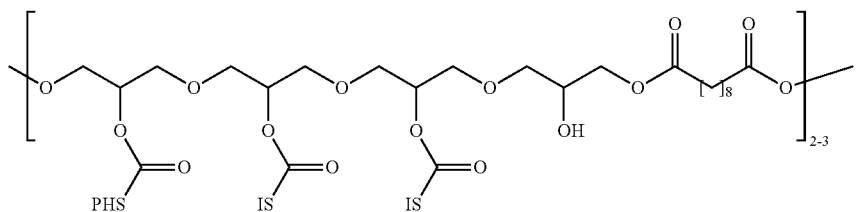

where PHS denotes polyhydroxystearic acid and IS denotes isostearic acid, and a hydrophobically modified polysaccharide chosen from hydroxy($C_1$-$C_3$)alkylcellulose modified with hydrophobic chains, in particular hydrophobic group(s) containing from 8 to 30 carbon atoms, preferably from 10 to 22 carbon atoms, in particular cetyl hydroxyethylcelluloses.

Additional Polysaccharides

The composition according to the invention may also comprise other additional polysaccharides, such as gums of plant or biotechnological origin.

Among the plant gums, mention may be made of guar gum and nonionic derivatives thereof (hydroxypropyl guar), gum Arabic, konjac or mannan gum, gum tragacanth, ghatti gum, karaya gum, carob gum; as examples, mention may be made of the guar gum sold under the name Jaguar HP105® by the company Rhodia; the mannan and Konjac® gum (1% glucomannan) sold by the company GfN, and the carob gum sold under the name Genu gum type RL200® by the company CP Kelko.

As gums of biotechnological origin, mention may be made of xanthan gum, such as Rhodicare XC® from Rhodia, and xanthan gums modified with glucose/mannose/glucuronic acid groups, such as Keltrol T® from CP Kelko, Rhodicare CFT® from Rhodia or Nomcort Z® from Nisshin Oil.

Mention will be made of xanthan gum as the preferred gum.

The content of additional polysaccharides may range from 0.01% to 20% by weight relative to the total weight of the composition, preferably from 0.2% to 5% by weight, and even more preferably from 0.5% to 2% by weight, relative to the total weight of the composition.

Fatty (Oily) Phase

The fatty or oily phase of the composition according to the invention generally represents from 5% to 50%, preferably from 8% to 40%, more preferably from 10% to 30%, and even more preferably from 15% to 25%, in particular from 10% to 25% by weight, relative to the total weight of the composition.

The fatty phase is constituted of oils and of all the other fatty substances and lipophilic constituents that may be present in the composition of the invention.

Mention may in particular be made of oils, fatty esters, waxes and butters, that may be, respectively, of natural (animal, plant) or synthetic origin.

Preferably, fatty substances of natural origin, such as plant oils, fatty esters of plant origin and waxes or butters of plant origin, will be used.

According to one preferred embodiment of the invention, the fatty phase contains at least one hydrocarbon-based oil of natural origin and/or at least one wax of natural origin.

The term "oil" is intended to mean a fatty substance that is liquid at ambient temperature (25° C.). Moreover, the term "hydrocarbon-based oil" is intended to mean a non-silicone oil, i.e. any oil comprising predominantly carbon and hydrogen atoms, and optionally ester, ether, fluoro, carboxylic acid and/or alcohol groups.

As hydrocarbon-based oils that can be used in the composition of the invention, mention may, for example, be made of:

hydrocarbon-based oils of animal origin, such as perhydrosqualene and squalane;

hydrocarbon-based oils of plant origin, such as liquid triglycerides of fatty acids containing from 4 to 10 carbon atoms, for instance heptanoic or octanoic acid triglycerides, or alternatively, for example, plant perhydrosqualene, sunflower oil, maize oil, rapeseed oil, soybean oil, marrow oil, grapeseed oil, sesame oil, hazelnut oil, apricot oil, macadamia oil, arara oil, castor oil, avocado oil, argan oil, virgin sweet almond oil, apricot kernel oil, rice bran oil, camellia oil, caprylic/capric acid triglycerides, such as those sold by the company Stearineries Dubois or those sold under the names Miglyol 810, 812 and 818 by the company Dynamit Nobel, jojoba oil and shea butter oil.

Preferably, jojoba oil, apricot kernel oil, and mixtures thereof, will be used.

As "fatty acid esters of plant or synthetic origin" mention may be in particular be made of esters and ethers, in particular of fatty acids, such as oils of formulae $R^1COOR^2$ and $R^1OR^2$ in which $R^1$ represents the residue of a fatty acid containing from 8 to 29 carbon atoms, and $R^2$ represents a branched or unbranched hydrocarbon-based chain containing from 3 to 30 carbon atoms, for instance purcellin oil, isononyl isononanoate, isopropyl myristate, isopropyl palmitate, 2-ethylhexyl palmitate (or octyl palmitate), 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; pentaerythritol esters, for instance pentaerythrityl tetraisostearate; lipophilic derivatives of amino acids, such as isopropyl lauroyl sarcosinate (INCI name: Isopropyl Lauroyl sarcosinate) sold under the name Eldew SL 205 by the company Ajinomoto.

Preferably, esters and ethers of which the fatty chains are of plant origin, for instance dicaprylyl carbonate (Cetiol CC) and dicaprylyl ether (Cetiol OE) from the company Cognis, will be used.

For the purpose of the present invention, the term "wax" is intended to mean a lipophilic fatty compound which is solid at ambient temperature (25° C.), with a solid/liquid reversible change of state, having a melting point of greater than or equal to 30° C., which may be up to 200° C., and a hardness of preferably greater than 0.5 MPa, and exhibiting, in the solid state, an anisotropic crystalline organization.

The hardness of the wax is determined by measuring the compression force, measured at 20° C. using a texturometer sold under the name TA-XT2i by the company Rheo, equipped with a stainless-steel cylinder 2 mm in diameter, which moves at the measuring speed of 0.1 mm/s, and which penetrates the wax to a penetration depth of 0.3 mm. In order to measure the hardness, the wax is melted at a temperature equal to the melting point of the wax +20° C. The molten wax is poured into a container 30 mm in diameter and 20 mm deep. The wax is recrystallized at ambient temperature (25° C.) for 24 hours, and is then stored for at least one hour at 20° C. before the hardness measurement is carried out. The value of the hardness is the compression force measured divided by the surface area of the texturometer cylinder in contact with the wax.

The wax used in the composition of the invention may in particular be chosen from waxes of animal origin, such as beeswax, lanolin and its derivatives; waxes of plant origin, such as candelilla wax, ouricuri wax, Japan wax, cork fibre wax, sugarcane wax, ricebran wax; microcrystalline waxes, such as the microcrystalline wax ($C_{20}$-$C_{60}$) sold under the name Microwax HW by the company Paramelt; hydrogenated oils that are solid at 25° C., such as hydrogenated jojoba oil, cottonseed oil; wax constituted of esters of olive oils and of fatty alcohols (such as the Phytowax range from the company Sophim), butters of plant origin, such as palm butter, cocoa butter and shea butter; shellac wax, montan wax, citrus fruit waxes, for instance orange wax or grapefruit wax, and mixtures thereof.

According to one particular embodiment of the invention, the wax is chosen from beeswax, carnauba wax, candelilla wax, butters of plant origin and shellac wax, and mixtures thereof.

More preferably, beeswax is used.

The amount of wax(es) may range, for example, from 0.2% to 10% by weight, preferably from 0.5% to 8% by weight, and better still from 1% to 5% by weight, relative to the total weight of the composition.

According to one preferred embodiment, the composition according to the invention is free of fatty substances of petrochemical origin and/or of synthetic origin (such as silicones or volatile oils of synthetic origin).

The expression "free of fatty substances of petrochemical or synthetic origin" is intended to mean that the composition comprises less than 1% by weight of fatty substances of petrochemical or synthetic origin relative to the total weight of the composition, in particular less than 0.5% by weight, preferably less than 0.1%, and even more preferably no fatty substances of petrochemical or synthetic origin.

According to one particular embodiment, the composition of the invention is free of silicones.

According to another embodiment, the composition of the invention is free of oils of synthetic origin, in particular of volatile oils of synthetic origin.

Aqueous Phase

The aqueous phase generally represents from 50% to 95% by weight relative to the total weight of the composition, preferably from 70% to 85% by weight relative to the total weight of the composition.

The aqueous phase generally contains water and hydrophilic adjuvants, among which are monoalcohols containing 2 to 8 carbon atoms, such as ethanol and isopropanol, and polyols such as glycerol and propane-diol, glycols such as pentylene glycol, propylene glycol, butylene glycol, isoprene glycol and polyethylene glycols such as PEG-8; sorbitol; sugars such as glucose, fructose, maltose, lactose or sucrose; and mixtures thereof.

The water may be a floral water such as cornflower water and/or a mineral water such as Vittel water, Lucas water or La Roche Posay water and/or a thermal spring water.

The polyol which is water-miscible at ambient temperature (25° C.) may be in particular chosen from polyols containing in particular from 2 to 20 carbon atoms, preferably containing from 2 to 10 carbon atoms, preferentially containing from 2 to 6 carbon atoms, such as glycerol, propylene glycol, butylene glycol, pentylene glycol, hexylene glycol, dipropylene glycol or diethylene glycol;

glycol ethers (containing in particular from 3 to 16 carbon atoms), such as mono-, di- or tripropylene glycol ($C_1$-$C_4$) alkyl ethers, or mono-, di- or triethylene glycol ($C_1$-$C_4$)alkyl ethers; and mixtures thereof.

The polyol which is water-miscible at ambient temperature may be in the composition at a content ranging from 1% to 20% by weight, relative to the total weight of the composition, and preferably ranging from 3% to 15% by weight.

The composition according to the invention may comprise a monoalcohol containing from 2 to 6 carbon atoms, such as ethanol or isopropanol, in particular at a content ranging from 0.01% to 10% by weight, relative to the total weight of the invention, and preferably ranging from 1% to 7% by weight.

The compositions according to the invention may be cosmetic or dermatological compositions. They will preferably be cosmetic compositions.

The composition according to the invention contains a physiologically acceptable medium.

In the present invention, the term "physiologically acceptable medium" is intended to mean a nontoxic medium which is compatible with the skin (including the inside of the eyelids), the mucous membranes, the hair or the lips of humans. A cosmetic composition is a product which has a pleasant appearance, odour and feel, and which is for topical application.

The composition according to the invention finds its use in a large number of treatments, in particular cosmetic treatments, for the skin, including the scalp, for the hair, for the nails and/or for the mucous membranes, in particular for caring for, cleansing and/or making up and/or anti-sun protection for the skin and/or the mucous membranes.

Thus, a subject of the present invention is the cosmetic use of the composition as defined above, for treating, protecting, caring for, removing makeup from and/or cleansing the skin, the lips and/or the hair, and/or for making up the skin and/or the lips.

A subject of the present invention is also a cosmetic treatment process for the skin, including the scalp, the hair and/or the lips, characterized in that a composition as defined above is applied to the skin, the hair and/or the lips.

In a known manner, the composition of the invention may also contain at least one cosmetic adjuvant chosen from cosmetic or dermatological active agents, preservatives, antioxidants, fragrances, fillers, pigments, UV screens, odour absorbers and dyestuffs.

The composition according to the invention advantageously contains at least one cosmetic or dermatological active agent.

The ingredients and/or active agents will be present in the composition at contents ranging from 0.01% to 20% by weight, preferably 0.05% to 10%, and even more preferably from 0.1% to 1% by weight, relative to the total weight of the composition.

These ingredients and/or active agents and also the concentrations thereof should be such that they do not modify the property desired for the composition of the invention.

Advantageously, ingredients and/or active agents of natural origin will be used.

As fillers that can be used in the composition of the invention, mention may, for example, be made of powders of natural organic materials, such as corn starch, wheat starch or rice starch; or else materials of natural mineral origin, for instance silica, talc, clays such as kaolin, montmorillonite, saponites, laponites and illites.

The amount of fillers is preferably less than or equal to 8% of the total weight of the composition, and better still less than or equal to 5% of the total weight of the composition. When they are present, these fillers may be in amounts ranging, for example, from 0.05% to 8% by weight, and preferably from 0.1% to 5% by weight, relative to the total weight of the composition.

According to one particular embodiment, the composition according to the invention comprises at least one active agent chosen from moisturizing agents; free-radical scavengers; keratolytic and desquamating agents; vitamins; anti-elastase and anti-collagenase agents; trace elements; extracts of algae or of plankton; enzymes and coenzymes; flavonoids and isoflavonoids; ceramides; anti-glycation agents; NO-synthase inhibitors; agents for stimulating the synthesis of dermal and/or epidermal macromolecules and/or for preventing their degradation; agents for stimulating fibroblast or keratinocyte proliferation and/or keratinocyte differentiation; tensioning agents; anti-pollution agents and/or free-radical scavengers; and muscle-relaxing or dermo-decontracting agents; and mixtures thereof.

The UV screens may be organic or inorganic.

As examples of organic screens active in the UV-A and/or UV-B range that can be added to the composition of the invention, mention may, for example, be made of anthranilates; cinnamic derivatives; dibenzoylmethane derivatives; salicylic derivatives; camphor derivatives; triazine derivatives such as those described in patent applications U.S. Pat. No. 4,367,390, EP863145, EP517104, EP570838, EP796851, EP775698, EP878469 and EP933376; benzophenone derivatives; β,β'-diphenylacrylate derivatives, benzotriazole derivatives, benzimidazole derivatives; imidazolines; the bisbenzoazolyl derivatives as described in patents EP669323 and U.S. Pat. No. 2,463,264; p-aminobenzoic acid (PABA) derivatives; the methylenebis(hydroxyphenylbenzotriazole) derivatives as described in applications U.S. Pat. No. 5,237,071, U.S. Pat. No. 5,166,355, GB2303549, DE19726184 and EP893119; screening polymers and screening silicones such as those described in particular in application WO 93/04665; dimers derived from α-alkylstyrene, such as those described in patent application DE19855649.

Mention may more particularly be made of the following UV screens, denoted below under their INCI name:

Para-Aminobenzoic Acid Derivatives:
  PABA,
  Ethyl PABA,
  Ethyl Dihydroxypropyl PABA,
  Ethylhexyl Dimethyl PABA sold in particular under the name Escalol 507 by the company ISP,
  Glyceryl PABA,
  PEG-25 PABA sold under the name Uvinul P25 by the company BASF.
Salicylic Derivatives:
  Homosalate sold under the name Eusolex HMS by the company Rona/EM Industries,
  Ethylhexyl Salicylate sold under the name Neo Heliopan OS by the company Haarmann and Reimer,
  Dipropylene glycol Salicylate sold under the name Dipsal by the company Scher,
  TEA Salicylate sold under the name Neo Heliopan TS by the company Haarmann and Reimer.
Dibenzoylmethane Derivatives:
  Butyl Methoxydibenzoylmethane sold in particular under the trade name Parsol 1789 by the company Hoffmann La Roche,
  Isopropyldibenzoylmethane.
Cinnamic Derivatives:
  Ethylhexyl methoxycinnamate sold in particular under the trade name Parsol MCX by the company Hoffmann La Roche,
  Isopropyl Methoxycinnamate,
  Isoamyl Methoxycinnamate sold under the trade name Neo Heliopan E 1000 by the company Haarmann and Reimer,
  Cinoxate,
  DEA Methoxycinnamate,
  Diisopropyl Methylcinnamate,
  Glyceryl Ethylhexanoate Dimethoxycinnamate.
β,β-Diphenylacrylate Derivatives:
  Octocrylene sold in particular under the trade name Uvinul N539 by the company BASF,
  Etocrylene sold in particular under the trade name Uvinul N35 by the company BASF.
Benzophenone Derivatives:
  Benzophenone-1 sold under the trade name Uvinul 400 by the company BASF,
  Benzophenone-2 sold under the trade name Uvinul D50 by the company BASF,
  Benzophenone-3 or Oxybenzone, sold under the trade name Uvinul M40 by the company BASF,
  Benzophenone-4 sold under the trade name Uvinul MS40 by the company BASF,
  Benzophenone-5,
  Benzophenone-6 sold under the trade name Helisorb 11 by the company Norquay;
  Benzophenone-8 sold under the trade name Spectra-Sorb UV-24 by the company American Cyanamid;
  Benzophenone-9 sold under the trade name Uvinul DS-49 by the company BASF,
  Benzophenone-12.
Benzylidenecamphor Derivatives:
  3-Benzylidenecamphor manufactured under the name Mexoryl SD by the company Chimex,
  4-Methylbenzylidenecamphor sold under the name Eusolex 6300 by the company Merck,
  Benzylidenecamphorsulphonic Acid manufactured under the name Mexoryl SL by the company Chimex,
  Camphorbenzalkonium Methosulphate manufactured under the name Mexoryl SO by the company Chimex,
  Terephthalylidenedicamphorsulphonic Acid manufactured under the name Mexoryl SX by the company Chimex,
  Polyacrylamidomethylbenzylidenecamphor manufactured under the name Mexoryl SW by the company Chimex.
Phenylbenzimidazole Derivatives:
  Phenylbenzimidazolesulphonic Acid sold in particular under the trade name Eusolex 232 by the company Merck,
  Benzimidazilate sold under the trade name Neo Heliopan AP by the company Haarmann and Reimer.
Triazine Derivatives:
  Anisotriazine sold under the trade name Tinosorb S by the company Ciba Geigy, Ethylhexyl triazone sold in particular under the trade name Uvinul T150 by the company BASF, Diethylhexyl Butamido Triazone sold under the trade name Uvasorb HEB by the company Sigma 3V.

Phenylbenzotriazole Derivatives:

Drometrizole Trisiloxane sold under the name Silatrizole by the company Rhodia Chimie, Methylenebisbenzotriazolyltetramethylbutylphenol sold in solid form under the trade name Mixxim BB/100 by the company Fairmount Chemical or in micronized form as an aqueous dispersion under the trade name Tinosorb M by the company Ciba Specialty Chemicals.

Anthranilic Derivatives:

Menthyl anthranilate sold under the trade name Neo Heliopan MA by the company Haarmann and Reimer.

Imidazoline Derivatives:

Ethylhexyl Dimethoxybenzylidene Dioxoimidazoline Propionate.

Benzalmalonate Derivatives:

Polyorganosiloxane comprising benzalmalonate functions, sold under the trade name Parsol SLX by the company Hoffmann La Roche, and mixtures of these screens.

The organic UV screens that are more particularly preferred are chosen from the following compounds:

Ethylhexyl Salicylate,
Butyl Methoxydibenzoylmethane,
Ethylhexyl Methoxycinnamate,
Octocrylene,
Phenylbenzimidazolesulphonic Acid,
Terephthalylidenedicamphorsulphonic Acid,
Benzophenone-3,
Benzophenone-4,
Benzophenone-5,
4-Methylbenzylidenecamphor,
Benzimidazolate,
Anisotriazine,
Ethylhexyl triazone,
Diethylhexyl Butamido Triazone,
Methylenebisbenzotriazolyltetramethylbutylphenol,
Drometrizole Trisiloxane,
and mixtures thereof.

The total amount of organic UV screens in the compositions according to the invention may range, for example, from 0.1% to 20% by weight relative to the total weight of the composition, and preferably ranges from 0.2% to 15% by weight relative to the total weight of the composition.

As inorganic screens that can be added to the composition of the invention, mention may, for example, be made of pigments and nanopigments of metal oxides, which may be coated or uncoated, in particular titanium oxide, iron oxide, zirconium oxide, zinc oxide or cerium oxide, and mixtures thereof, it being possible for these oxides to be in the form of optionally coated microparticles or nanoparticles (nanopigments).

Titanium dioxide will preferably be used.

The UV screens may be present in an amount with respect to active material ranging from 0.01% to 20% by weight of active material, preferably from 0.1% to 15% by weight, and better still from 0.2% to 10% by weight, relative to the total weight of the composition.

As examples of active agents, mention may, for example, be made of (N-2-hydroxyethylpiperazine-N-2-ethane)sulphonic acid (HEPES); hyaluronic acid; lanolin; urea, mixtures containing urea, such as NMF (Natural Moisturizing Factor), and urea derivatives such as N-(2-hydroxyethyl)urea (Hydrovance from the company National Starch); 2-oxothiazolidine-4-carboxylic acid (procysteine); α-hydroxy acids, in particular fruit-derived acids, for instance glycolic acid, lactic acid, malic acid, citric acid, tartaric acid or mandelic acid, derivatives thereof and mixtures thereof; β-hydroxy acids, for instance salicylic acids and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate, magnesium ascorbyl phosphate or sodium ascorbyl phosphate; its esters, for instance ascorbyl acetate, ascorbyl palmitate and ascorbyl propionate, or its sugars, for instance glycosylated ascorbic acid, and mixtures thereof; β-keto acids; retinoids such as retinol (vitamin A) and its esters, retinal, retinoic acid and its derivatives, and also the retinoids described in documents FR-A-2,570,377, EP-A-199 636, EP-A-325 540, EP-A-402 072, EP-A-325 540 and EP-A-402 072; carotenoids such as lycopene; ceramides; sapogenins and plant extracts containing them, in particular extracts of wild yam; resveratrol; pseudo-dipeptides such as {2-[acetyl-(3-trifluoromethyl-phenyl)amino]-3-methylbutyrylamino}acetic acid; vitamins such as, for example, in addition to vitamin A and vitamin C indicated above, vitamin E (tocopherol), vitamin B3 (or vitamin PP or niacinamide), vitamin B5 (panthenol in its various forms: D-panthenol, DL-panthenol), vitamin D, vitamin F (mixture of essential fatty acids), derivatives, precursors and analogues of these vitamins; soybean extracts, in particular soybean protein hydrolysates or soybean extracts rich in isoflavones; trace elements such as copper, zinc, selenium, iron, magnesium or manganese; extracts of algae, such as the product sold under the name Stimoderm by the company CLR; extracts of plankton such as the plankton in an aqueous dispersion (CTFA name: *Vitreoscilla* Ferment) sold under the name Mexoryl SAH by the company Chimex; enzymes; coenzymes such as ubiquinone or coenzyme Q10 which belongs to the alkylenated-chain benzoquinone family, coenzyme R which is biotin (or vitamin H); yeast extracts such as the extract of *S. cerevisiae* sold under the name Cytovitin LS 9388 by Laboratoires Sériobiologiques; adenosine; plant extracts such as extract of licorice; calmatives such as bisabolol and calming plant extracts, for instance extracts of rose (*Rosa gallica*) and extracts of mint (*Mentha piperita*); and any active agent suitable for the final purpose of the composition, and mixtures thereof.

The cosmetic composition according to the invention finds its use in a very large number of cosmetic treatments for the skin, including the scalp, and the mucous membranes (lips), in particular for caring for and/or treating dry and/or sensitive skin.

According to one particular embodiment, the composition finds a use in the treatment of the signs of skin ageing, especially for reducing the visible or tactile irregularities of the surface of the skin, in particular for reducing wrinkles, fine lines and blemishes on the skin, for smoothing the skin and for unifying the skin complexion.

Thus, a subject of the present invention is the cosmetic use of the composition as defined above, for skincare, in particular for treating the signs of skin ageing.

A subject of the present invention is also a nontherapeutic process for caring for, making up or removing makeup from the skin, including the scalp, the hair and/or the lips, comprising the application to the skin, the hair and/or the lips of a composition according to the invention.

In the care field, the compositions are particularly suitable for treating the signs of ageing, such as wrinkles;

as a care product for treating dry and/or sensitive skin.

A subject of the present invention is also a cosmetic process for reducing the visible or tactile irregularities of the surface of the skin, in particular for reducing wrinkles and fine lines and/or blemishes on the skin and/or smoothing and/or firming the skin and/or unifying the complexion, comprising the topical application to the skin of a composition as defined above.

The invention also relates to the use of the combination according to the invention of a fatty acid ester of a polyol and of at least one hydrophobically modified polysaccharide chosen from inulins, celluloses and derivatives thereof, starches and agars, and mixtures thereof, for the preparation of a pharmaceutical composition for use in treating skin disorders.

The examples hereinafter of compositions according to the invention are given by way of illustration without being limiting in nature. The compounds are indicated by a chemical name or by an INCI name. The amounts are given therein as % by weight, unless otherwise mentioned.

EXAMPLE 1

Comparative Examples of Stability

Examples B and C are prepared according to the invention. Example A is the comparative example.

| | Composition | Ex. A | Ex. B | Ex. C |
|---|---|---|---|---|
| Aqueous phase | Preservative | 0.2 | 0.2 | 0.2 |
| | Glycerol | 3 | 3 | 3 |
| | Magnesium sulphate | 1.5 | 1.5 | 1.5 |
| | Water | qs 100 | qs 100 | qs 100 |
| | Cetyl hydroxyethyl-cellulose (Polysurf 67 from the company Aqualon) | | 1 | |
| | Inulin lauryl carbamate (Inutec SP1 from the company Orafti) * | | | 0.9 |
| Oily phase | Polyglyceryl-4 diisostearate/polyhydroxystearate (Isolan GPS from the company Goldschmidt) | 3 | 3 | 3 |
| | Hydrogenated castor oil | 0.1 | 0.1 | 0.1 |
| | Microcrystalline wax | 0.1 | 0.1 | 0.1 |
| | Diethylhexyl carbonate | 9.8 | 9.8 | 9.8 |
| | Ethylhexyl palmitate | 11 | 11 | 11 |
| stability Results | | Unstable | Stable | Stable |

* = Inutec SP1 from the company Orafti containing 96.5% by weight of active material of inulin lauryl carbamate.

Implementation: preparation of the aqueous phase by dispersion of the constituents in water with stirring at 80° C. Preparation of the oily phase by mixing the constituents at 70-80° C.

Emulsification by dispersion of the aqueous phase in the oily phase under hot conditions (70-80° C.) with stirring in a Moritz-type turbine.

Shiny white creams are obtained.

Stability: The emulsion according to Example A undergoes phase separation during the centrifugation and over time. The phase separation is totally unacceptable after 2 months at 37° C. and 45° C. and also during −20°/+20° C. heat cycles.

Emulsions B and C on the other hand are stable under the same conditions.

Sensory properties: Products B and C are more creamy and are soft to the touch compared with product A.

In the case of trial C, we also have a greater feeling of freshness compared with trial A.

EXAMPLE 2

Formulation Examples

| Soothing cream | | |
|---|---|---|
| | | % |
| Aqueous phase | Preservative | 0.2 |
| | Glycerol | 5 |
| | Magnesium sulphate | 1.5 |
| | Cetyl hydroxyethylcellulose (Polysurf 67 from the company Aqualon) | 1 |
| | Water | qs 100 |
| Oily phase | Polyglyceryl-4 diisostearate/polyhydroxystearate (Isolan GPS from the company Golschmidt) | 3 |
| | Dicaprylyl ether | 8 |
| | Dicaprylyl carbonate | 6 |

| Emollient cream | | |
|---|---|---|
| | | % |
| Aqueous phase | Preservative | 0.2 |
| | Glycerol | 5 |
| | Magnesium sulphate | 1.5 |
| | Water | qs 100 |
| Oily phase | Polyglyceryl-4 diisostearate/polyhydroxystearate (Isolan GPS from the company Golschmidt) | 3 |
| | Dicaprylyl ether | 9 |
| | Dicaprylyl carbonate | 4.5 |
| | Beeswax | 0.2 |
| | Inulin lauryl carbamate (Inutec SP1)* | 0.5 |

*Inutec SP1 from the company Orafti containing 96.5% by weight of active material of inulin lauryl carbamate.

Procedure

Emulsification by slow dispersion of the aqueous phase in the oily phase at 70° C. Creams which are supple and rich when applied, leaving the skin soft, smooth and comfortable, are obtained.

The invention claimed is:

1. A composition in the form of a water-in-oil emulsion comprising an aqueous phase dispersed in an oily phase and comprising:

fatty acid ester of a polyol present in the composition at a content ranging from 0.5% to 15%, relative to the total weight of the composition in which the fatty acid ester of a polyol is polyglyceryl-4 diisostearate/polyhydroxystearate/sebacate of formula

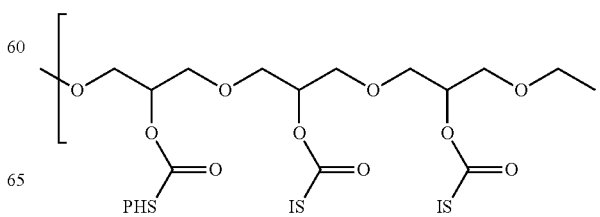

-continued

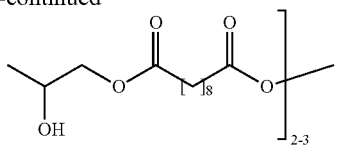

where PHS denotes polyhydroxystearic acid and IS denotes isostearic acid
and
Inulin lauryl carbamate present at a content ranging from 0.01% to 20% by weight relative to the total weight of the composition, wherein the composition is free of silicones and free of volatile oils of synthetic origin.

2. A composition according to claim 1, wherein the oily phase is present in the composition at a content ranging from 10% to 30%, relative to the total weight of the composition.

3. A nontherapeutic process for caring for, making up or removing makeup from the skin, comprising the application to the skin, the hair and/or the lips, of a composition as defined in claim 1.

4. A process for reducing the visible or tactile irregularities of the surface of the skin, comprising the topical application to the skin of the composition as defined in claim 1.

5. A composition according to claim 1, in which the fatty acid ester of a polyol is present in the composition at a content ranging from 1% to 5%, relative to the total weight of the composition.

6. A composition according to claim 1, in which the fatty acid ester of a polyol is present in the composition at a content ranging from 1.5% to 3.5%, relative to the total weight of the composition.

7. A composition according to claim 1, wherein the inulin lauryl carbamate is present at a content ranging from 0.05% to 15% by weight relative to the total weight of the composition.

8. A composition according to claim 1, wherein the inulin lauryl carbamate is present at a content ranging from 0.1% to 5% by weight relative to the total weight of the composition.

9. A composition according to claim 1, wherein the inulin lauryl carbamate is present at a content ranging from 0.5% to 3% by weight relative to the total weight of the composition.

10. A composition according to claim 1, wherein the inulin lauryl carbamate is present at a content ranging from 0.1% to 3% by weight relative to the total weight of the composition.

11. A composition according to claim 1, wherein the emulsion does not undergo phase separation after two months at 37° C.

* * * * *